(12) United States Patent
Salib

(10) Patent No.: US 6,436,031 B1
(45) Date of Patent: Aug. 20, 2002

(54) MASCULINE BRACE

(76) Inventor: George F. Salib, 152 Church Street, Grand Falls, New Brunswick (CA), E3Z 2P2

(*) Notice: Subject to any disclaimer, the term of this patent is extended or adjusted under 35 U.S.C. 154(b) by 97 days.

(21) Appl. No.: 09/704,713

(22) Filed: Nov. 3, 2000

(51) Int. Cl.$^7$ .................................................. A61F 5/00
(52) U.S. Cl. ....................................................... 600/39
(58) Field of Search .................... 600/38–41; 602/18, 602/22, 26, 5–6; 128/846, 882; 2/161.1; 482/48

(56) References Cited

U.S. PATENT DOCUMENTS

| | | |
|---|---|---|
| 853,410 A | 5/1907 | Huebner |
| 1,362,398 A | 12/1920 | Crawford et al. |
| 1,585,861 A | 5/1926 | Huff |
| 3,495,588 A | 2/1970 | Walters ........................ 128/79 |
| 3,920,007 A | 11/1975 | Line ............................. 128/79 |
| 4,074,712 A | 2/1978 | Wright ......................... 128/79 |
| 4,262,662 A | 4/1981 | Allinson ....................... 128/79 |
| 4,262,663 A | 4/1981 | Allinson et al. ............... 128/79 |
| 4,449,521 A | 5/1984 | Panzer ......................... 128/79 |
| 4,653,484 A * | 3/1987 | Cannon ........................ 600/39 |
| 4,672,954 A | 6/1987 | Panzer ......................... 128/79 |
| 4,813,406 A * | 3/1989 | Ogle, II ....................... 602/22 |
| 4,872,447 A | 10/1989 | Tsirjulnikov et al. ......... 128/79 |
| 5,065,744 A | 11/1991 | Zusmanovsky .............. 128/79 |
| 5,413,554 A * | 5/1995 | Trueman ...................... 482/48 |
| 5,584,799 A * | 12/1996 | Gray ............................ 602/18 |
| 5,782,780 A * | 7/1998 | Mason et al. ................. 602/26 |
| 5,785,057 A * | 7/1998 | Fischer ........................ 128/846 |
| 5,800,340 A | 9/1998 | Gekhter et al. ............... 600/39 |
| 5,836,902 A * | 11/1998 | Gray ............................ 128/882 |
| 5,911,686 A | 6/1999 | Kohut .......................... 600/38 |
| 5,921,945 A * | 7/1999 | Gray ............................ 128/882 |
| 5,963,985 A * | 10/1999 | Behr et al. .................... 2/161.1 |

FOREIGN PATENT DOCUMENTS

| | | |
|---|---|---|
| CA | 1157331 | 11/1983 |
| RU | 2003307 | 11/1993 |
| SU | 1826885 | 7/1993 |

* cited by examiner

*Primary Examiner*—Eric F. Winakur
*Assistant Examiner*—Nikita Veniaminov
(74) *Attorney, Agent, or Firm*—Mario Theriault

(57) ABSTRACT

In the present invention, there is provided a masculine brace having a stiff splint member which has an elongated channel configuration, a rear end and a front end. A first pair of straps extends from the rear end of the stiff splint member and jointly define a rear circular clamp oriented transversely relative to the stiff splint member for clamping a penis at its base. A second pair of straps extends from an intermediate region along the stiff splint member at a distance from the first pair of straps, and jointly define a front circular clamp oriented transversely relative to the stiff splint member for clamping a penis at an intermediate region thereof. The masculine brace also comprises a bulb affixed to the front end of the stiff splint member. The bulb has a circular projection in line with the front and rear circular clamps.

20 Claims, 7 Drawing Sheets

MASCULINE BRACE

FIELD OF THE INVENTION

This invention pertains to surgical splints for supporting a flaccid penis in an erected attitude during sexual intercourse, and more particularly, it pertains to a male brace that has smooth surfaces and resilient straps which are operable with one hand for easy installation or removal of the brace.

BACKGROUND OF THE INVENTION

Male braces are used by those suffering from erectile dysfunction affections and are alternatives to medication, vigour-enhancing vitamins, surgical interventions and inflatable implants. There are numerous devices to available in the prior art which are usable by males in order to improve their abilities to participate in a sexual intercourse. Some of these devices are described in the following documents:

U.S. Pat. No. 853,410, issued on May 14, 1907 to E. D. Huebner;
U.S. Pat. No. 1,362,398, issued on Dec. 14, 1920 to L. H. Crawford et al.;
U.S. Pat. No. 1,585,861, issued on May 25, 1926 to W. H. Huff,
U.S. Pat. No. 3,495,588, issued on Feb. 17, 1970 to R. S. Walters;
U.S. Pat. No. 3,920,007, issued on Nov.18, 1975 to R. M. Line;
U.S. Pat. No. 4,074,712, issued on Feb. 21, 1978 to A. F. Wright;
U.S. Pat. No. 4,262,662, issued on Apr. 21, 1981 to F. W. Allinson;
U.S. Pat. No. 4,262,663, issued on Apr. 21, 1981 to F. W. Allinson;
U.S. Pat. No. 4,449,521, issued on May 22, 1984 to J. S. Panzer;
U.S. Pat. No. 4,672,954, issued on Jun. 16, 1987 to J. S. Panzer;
U.S. Pat. No. 4,872,447, issued on Oct. 10, 1989 to M. V. Tsirjulnikov et al.;
U.S. Pat. No. 5,065,744, issued on Nov. 19, 1991 to Z. A. Zusmanovsky;
U.S. Pat. No. 5,800,340, issued on Sep. 1, 1998 to V. Gekhter et al.;
U.S. Pat. No. 5,911,686, issued on Jun. 15, 1999 to J. Kohut;
Russian document SU 1,826,885 published in July 1993;
Russian document RU 2,003,307 published in November 1993.

It is believed that the prior art devices have been used in the past with varying degrees of success. It is believed that the limited success of these devices is due to the fact that some of these braces have protruding clips, hinges and other ferrules which tend to irritate the skin of the user or of his partner. Some devices of the prior art have converging surfaces at either extremity relative to the longitudinal axis thereof. These converging surfaces tend to pinch the skin during sexual intercourse or catch pelvis hair, resulting in much discomfort to the user or to his partner. Some other prior devices comprise rod-like elements and bendable components, the installation of which requires intricate manipulations that are only understood by the mechanically-minded individuals.

As such, it may be appreciated that there continues to be a need for a new and improved male brace which does not have any protruding edges or converging surfaces relative to the longitudinal axis thereof, and which has a self-explanatory structure that is usable without instruction.

SUMMARY OF THE INVENTION

The present invention provides a masculine brace for supporting a flaccid penis during sexual intercourse. The masculine brace has soft and smooth shapes free of crevices and sharp edges. The masculine brace has a self-explanatory appearance and is manufacturable in various sizes and in configurations that are operable with one hand.

In a first aspect of the present invention, there is provided a masculine brace having a stiff splint member which has an elongated channel configuration, a rear end and a front end. A first pair of straps extends from the rear end of the stiff splint member and jointly define a rear circular clamp oriented transversely relative to the stiff splint member for clamping a penis at its base. A second pair of straps extends from an intermediate region along the stiff splint member at a distance from the first pair of straps, and jointly define a front circular clamp oriented transversely relative to the stiff splint member for clamping a penis at an intermediate region thereof. The masculine brace also comprises a bulb affixed to the front end of the stiff splint member. The bulb has a circular projection in line with the front and rear circular clamps.

The principal advantages of the masculine brace according to the present invention are that the front and rear circular clamps are usable for holding the stiff splint member against a lower region of a penis for supporting the penis in an erected attitude, and the stiff splint member and the bulb are usable for simulating an action of an erected penis when that penis is affected by an erectile dysfunction affection.

In another feature of the present invention, the material of construction of the masculine brace comprises a skeletal structure made of a rigid and resilient material and a coating made of a soft, smooth and sanitary material. The masculine brace is manufacturable in various sizes and various stiffness.

In another aspect of the present invention, the straps in the first and second pairs of straps comprise inside straps and outside straps, and the inside straps are joined to each other by a tendon. The straps in the front and second pairs of straps are thereby operable simultaneously with one hand.

In another aspect of the present invention, one of the rear straps supports a pubis cushion that is usable in cooperation with the symphysis bone of the user to generate thrust.

In yet another aspect of the present invention, the first and second straps extend helically from an intermediate region of the stiff splint member in a cross-over arrangement, toward the rear end of the stiff splint member. The first and second straps define with the stiff splint member a cylindrical clamping cavity, for simultaneously clamping a penis along a mid-region and a base thereof. This feature of the present invention is advantageous for allowing the operation of the straps using one hand, working near the rear end of the masculine brace.

In yet a further feature of the present invention, the masculine brace also comprises a U-shaped thrust flange mounted to the rear end of the stiff splint member. The thrust flange adds comfort and convenience to the use of the masculine brace.

Other advantages and novel features of the present invention will become apparent from the following detailed description.

BRIEF DESCRIPTION OF THE DRAWINGS

Three embodiments of the present invention are illustrated in the accompanying drawings, in which like numerals denote like parts throughout the several views, and in which.

DETAILED DESCRIPTION OF THE PREFERRED EMBODIMENT

Figure 1:
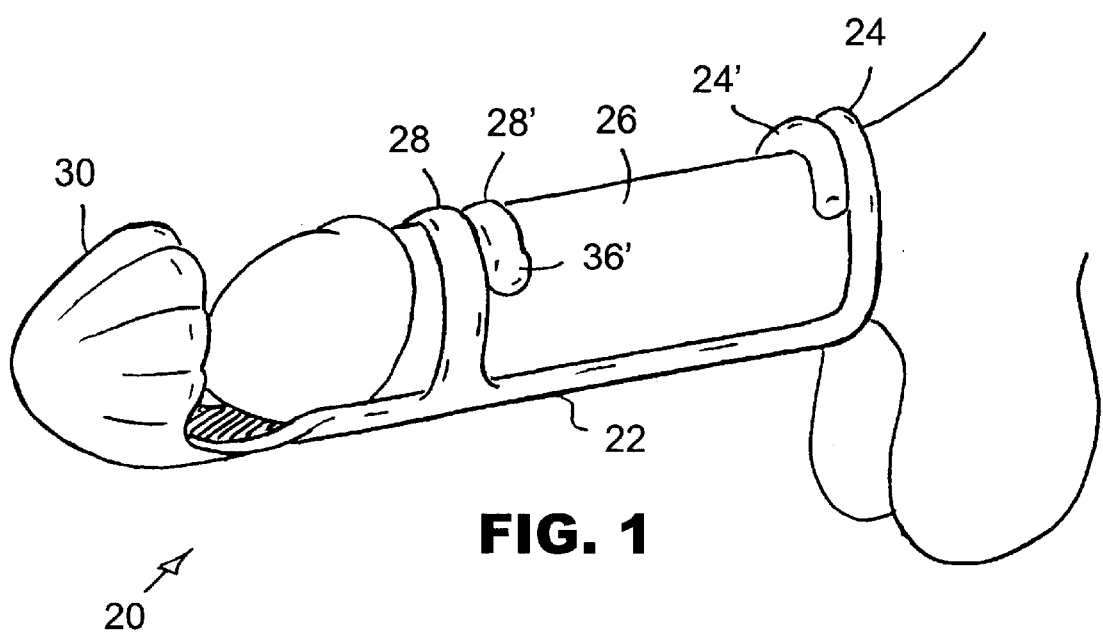
FIG. 1 is a perspective view of the masculine brace according to the first preferred embodiment.

While this invention is susceptible of embodiments in many different forms, there is shown in the drawings and will be described in details herein three specific embodiments of the invention, with the understanding that the present disclosure is to be considered as an example of the principles of the invention and is not intended to limit the invention to the embodiments illustrated.

Figure 2:
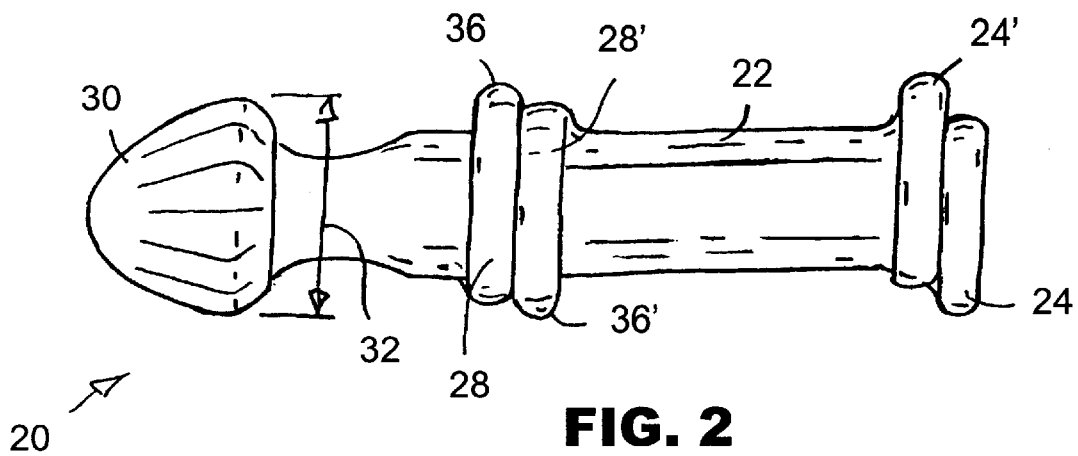
FIG. 2 is a top view of the masculine brace according to the first preferred embodiment.
Figure 3:
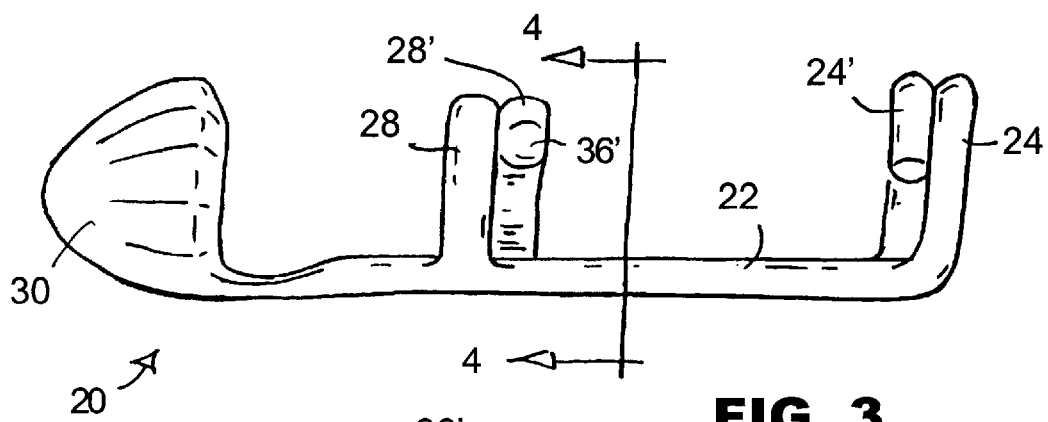
FIG. 3 is a side view of the masculine brace according to the first preferred embodiment.

Referring firstly to FIGS. 1 to 3, the structure and best mode of operation of the masculine brace 20 according to the first preferred embodiment of the present invention are illustrated therein.

The masculine brace 20 comprises broadly, a stiff splint member 22, a first pair of straps 24, 24' extending from the rear end of the stiff splint member 22 for circling a penis 26 at its base, and a second pair of straps 28, 28' extending from an intermediate region of the stiff splint member 22, for circling an intermediate region of a penis 26. The spacing between the two pairs of straps is preferably such that the second straps 28, 28' are positional adjacent the glans on a penis as illustrated in FIG. 1. The front end of the stiff splint member 22, is integrated with a resilient bulb 30, which is shaped to simulate an enlarged glans. The stiff splint member 22 is mounted at right angle with the circumference of the bulb 30 and is tangent with the outside surface of the bulb 30. The bulb 30 has a circular projection 32 which is substantially in line with the alignment and the overall diameter of the circular clamps defined by the first and second pairs of straps.

Figure 4:
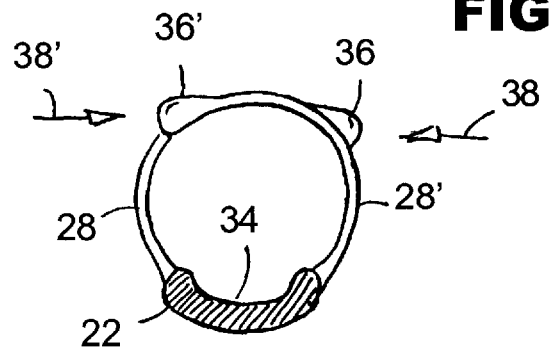
FIG. 4 is a cross-section view through the masculine brace according to the first preferred embodiment taken along line 4—4 in FIG. 3.

Referring now to FIG. 4 the stiff splint member 22 preferably has a channel-shaped cross-section and a trough 34 along the inside surface thereof for conforming to the cross-section of a penis.

Also in reference to FIG. 4 in particular, the straps 24, 24' and 28, 28', are preferably integrally molded with the stiff splint member 22 and extend from the longitudinal edges of the splint member 22. Each strap has a substantially semi-circular shape and the straps in each pair extend beside each other as to enclose a penis 26 completely. The end of at least each strap in the second pair of straps 28, 28' has a rounded bulge 36, 36' formed thereon. These bulges or beads are particularly useful for enlarging a clamping circle defined by the straps, by applying forces thereon in opposite directions as indicated by the arrows 38, 38' in FIG. 4. When both pairs of straps are pressed in this manner, the masculine brace 20 is easily installed for use.

The preferred material of construction of the stiff splint 22 is a soft, non-irritating and non-absorbent plastic material being unbreakable and having a stiffness which is at least as much as the stiffness of an erected penis, but not substantially more.

The preferred material of construction of the straps is also a soft, non-irritating and non-absorbent plastic material having a thin crosssection, resilience and shape-memory properties, such that each strap retains its original shape and clamping ability during use of the masculine brace 20.

The preferred material of construction of the bulb 30 is a soft, nonirritating, non-absorbent and elastic material having a firmness similar to that of an erected penis, but not substantially more.

The preferred firmness of the bulb 30 mentioned above as well as the aforesaid preferred stiffness of the splint member 22, are sufficient for their intended functions but not substantially more in order to prevent any discomfort to the user as well as to the partner of the user.

The plastic and elastic materials mentioned hereinbefore are teflon, silicon, latex or similar soft, smooth and sanitary material. The material of construction of the masculine brace 20 can also include a skeletal structure or a core made with resilient plastic or stainless steel and coated with teflon, silicon, latex or similar soft, smooth and sanitary material.

All surfaces of the masculine brace 20 are formed with large radii, without crevice, metal part or sharp edge and converging surface relative to the longitudinal axis thereof. All surfaces are soft and smooth to the touch. As can be appreciated, the shapes of the parts and the overall structure of the masculine brace 20 makes it particularly advantageous for use with a condom if desired.

The masculine brace 20 is preferably manufactured in different sizes with different clamping diameters, different lengths, different spacings between the pair of straps, different sizes of bulbs and different stiffness.

It will be appreciated that the clamping diameter defined by the first pair of straps 24, 24' may be slightly smaller than the clamping diameter defined by the second pair of straps 28, 28' to provide a slightly tighter clamping effect at the base of a penis 26, and to prevent a premature softening of an erected penis affected by an erectile dysfunction affection.

Figure 5:
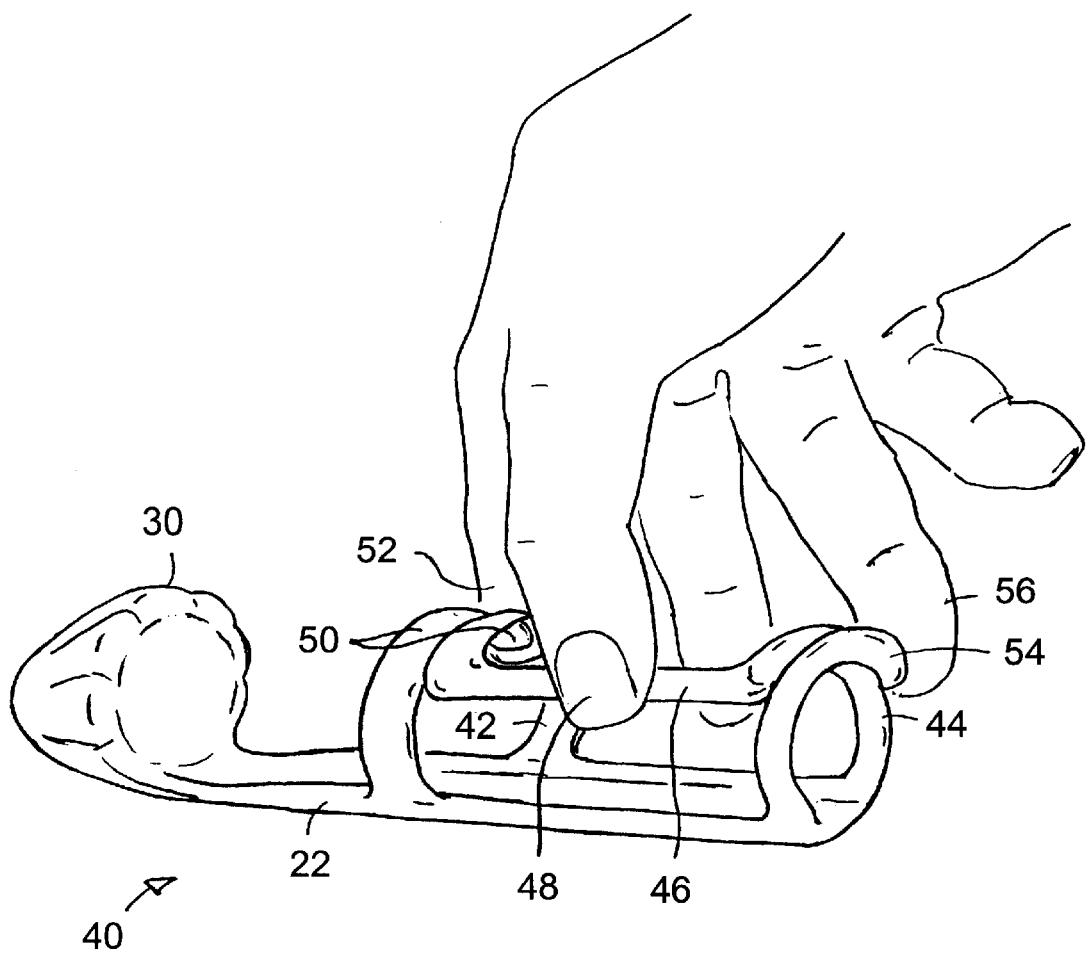
FIG. 5 is a perspective view of the masculine brace according to the second preferred embodiment.

Referring now to FIG. 5, there is shown therein a second embodiment of the preferred masculine brace which does not differ substantially from the first preferred embodiment. The second preferred embodiment 40 has a stiff splint member, a resilient bulb and two pairs of straps for retention thereof to a penis, as previously explained. The straps in each pair are oriented in opposite directions.

In the second preferred embodiment 40, the inside straps 42, 44 in the front and rear pair of straps respectively are oriented in a same direction and are joined to each other by a longitudinal tendon 46. The longitudinal tendon 46 is particularly advantageous for installing the masculine brace 40 with one hand as illustrated in FIG. 5.

The installation of the masculine brace 40 according to the second preferred embodiment is preferably effected by pressing the tendon 46 with the thumb 48 in one direction while pressing the outside strap 50 on the front pair of straps with the index finger 52 and pressing the outside strap 54 on the rear pair of straps with the third finger 56, in the opposite direction to simultaneously stretch out and enlarge the clamping diameters of both pairs of straps. The masculine brace 40 is then easily slipped over and installed over a penis. The removal of the masculine brace 40 is similarly effected.

Figure 6:
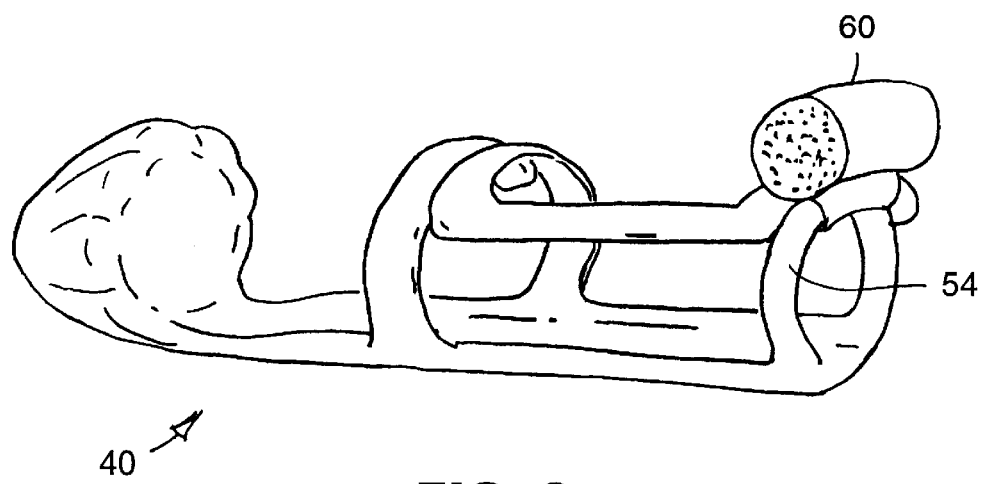
FIG. 6 is another perspective view of the masculine brace according to the second preferred embodiment having a pubis cushion mounted thereon.
Figure 7:
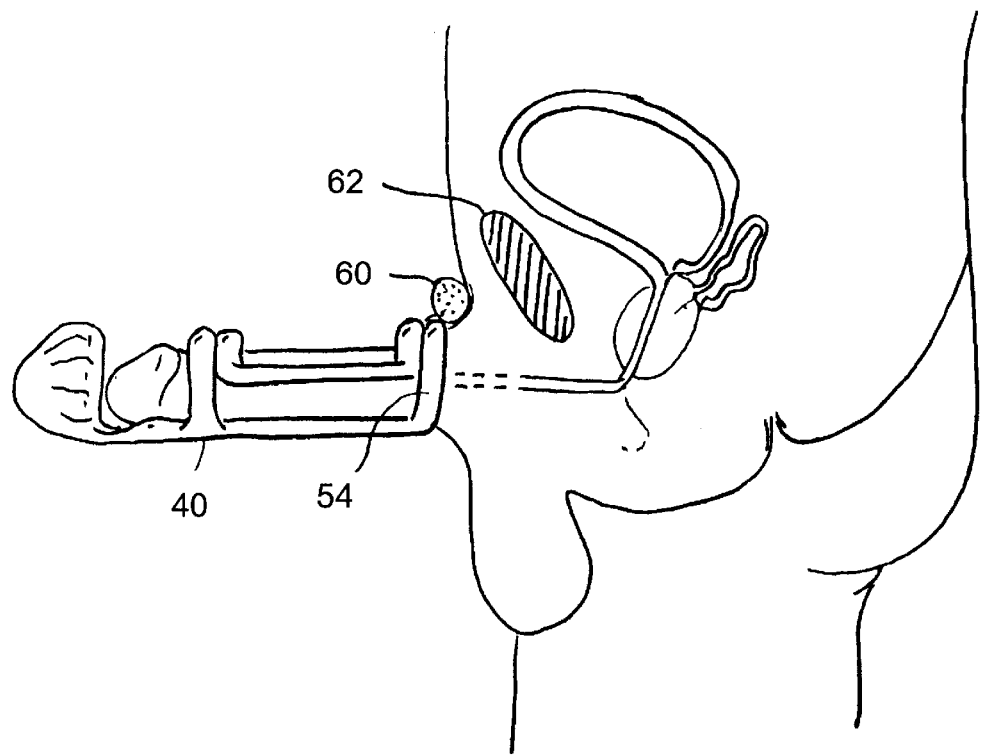
FIG. 7 illustrate an installation of the masculine brace according to the second preferred embodiment and a preferred positioning of the pubis cushion adjacent the symphysis bone of a user.
Figure 8:
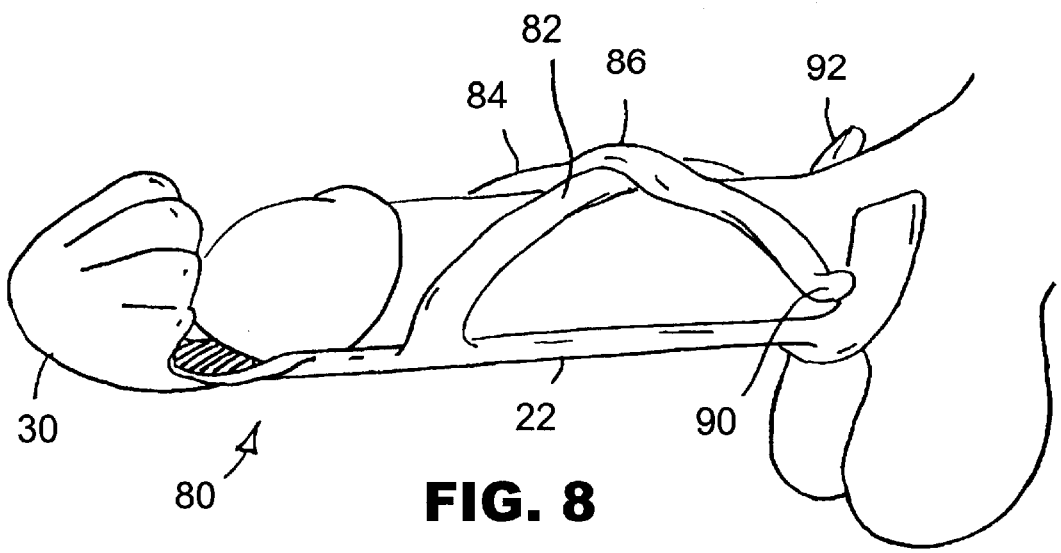
FIG. 8 is a perspective view of the masculine brace according to the third preferred embodiment of the present invention, in an installed mode.
Figure 9:
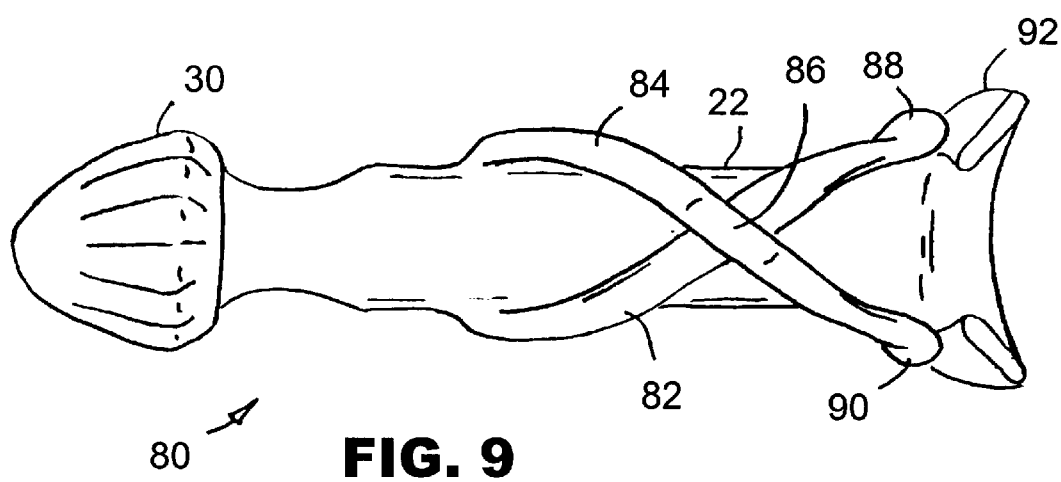
FIG. 9 illustrates a top view of the masculine brace according to the third preferred embodiment.
Figure 10:
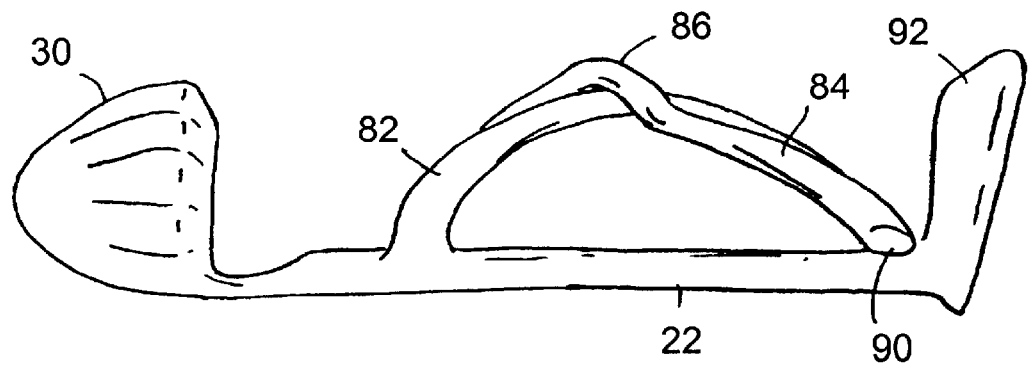
FIG. 10 illustrates a side view of the masculine brace according to the third preferred embodiment.

Referring now to FIGS. 6 and 7, the masculine brace according to the second preferred embodiment is usable with a pubis cushion 60 mounted over the outside strap 54. The pubis cushion 60 is made of a sponge-like material and its use allows the user of the masculine brace 40 to use his body, through the symphysis bone 62 acting against the pubis cushion 60 to generate the thrust that simulates the natural act.

In FIGS. 8 to 11 there are illustrated several views of the masculine brace according to the third preferred embodiment 80. The third embodiment is similar to the first and second preferred embodiments as all three braces have a splint member 22, a bulb 30 similarly mounted to the end of the splint member and soft and smooth surfaces. The masculine brace according to the third preferred embodiment 80, however, has a pair of helical straps 82, 84 extending from an intermediate region along the splint member 22 to the rear end of the splint member and crossing over each other substantially at a mid-point thereof. The helical straps 82, 84 define with the splint member 22 a cylindrical clamping cavity similar to the first and second embodiments and as can be understood from FIG. 4, wherein the cross-over point 86 of the straps is opposite the splint member 22. The helical straps 82, 84 constitute a variant of the first and second preferred embodiments in that they define with the splint member 22 a cylindrical clamping cavity for simultaneously clamping a penis at a midregion and at a base thereof. Each of straps 82, 84 has on its rear end a raised tab, labelled as 88 and 90 respectively. The masculine brace 80 further has a U-shaped trust flange 92 mounted to the rear end of the splint member 22 adjacent the raised tabs 88, 90. The thrust flange 92 is made of a soft, smooth and sanitary material that has slightly less stiffness than the splint member 22, relative to their respective purposes.

Figure 11:
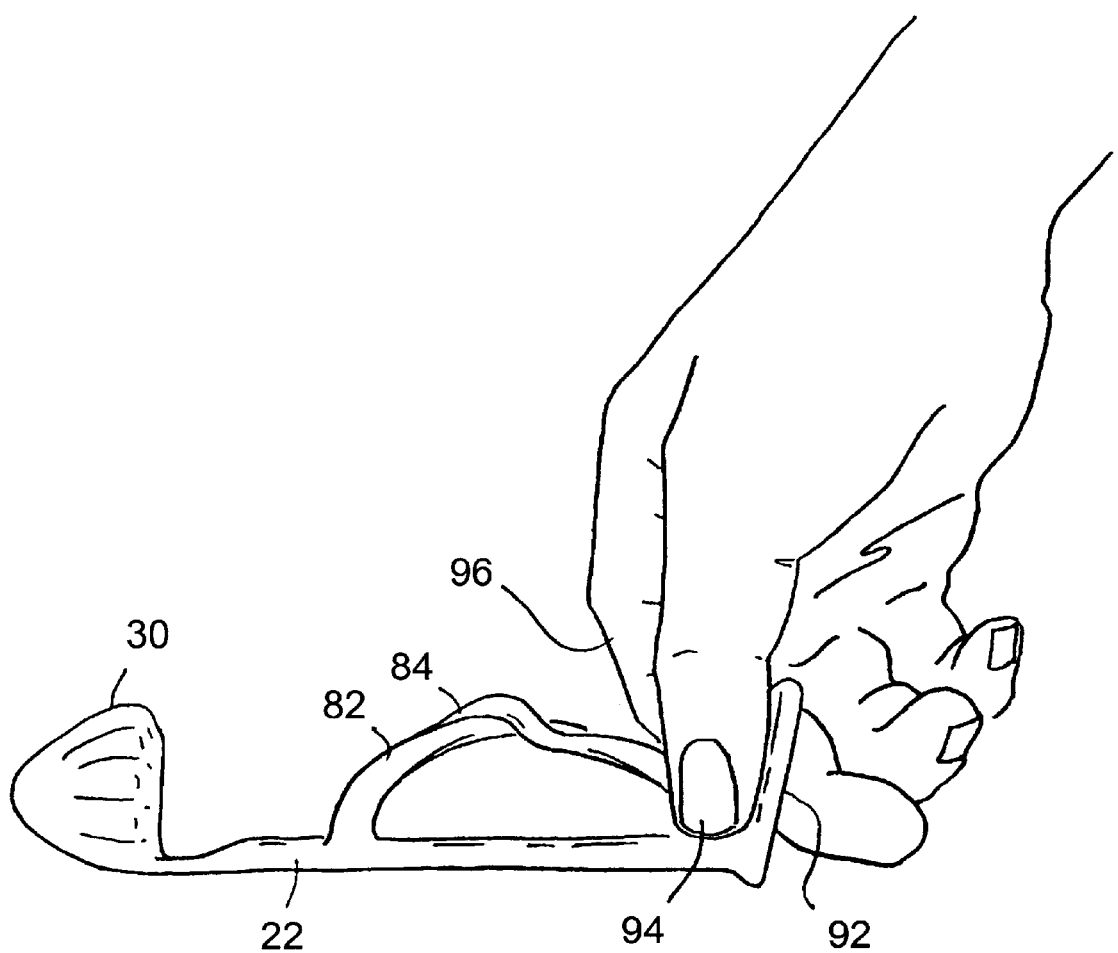
FIG. 11 illustrates another side view of the masculine according to the third preferred embodiment and a preferred method of installation thereof.
Figure 12:
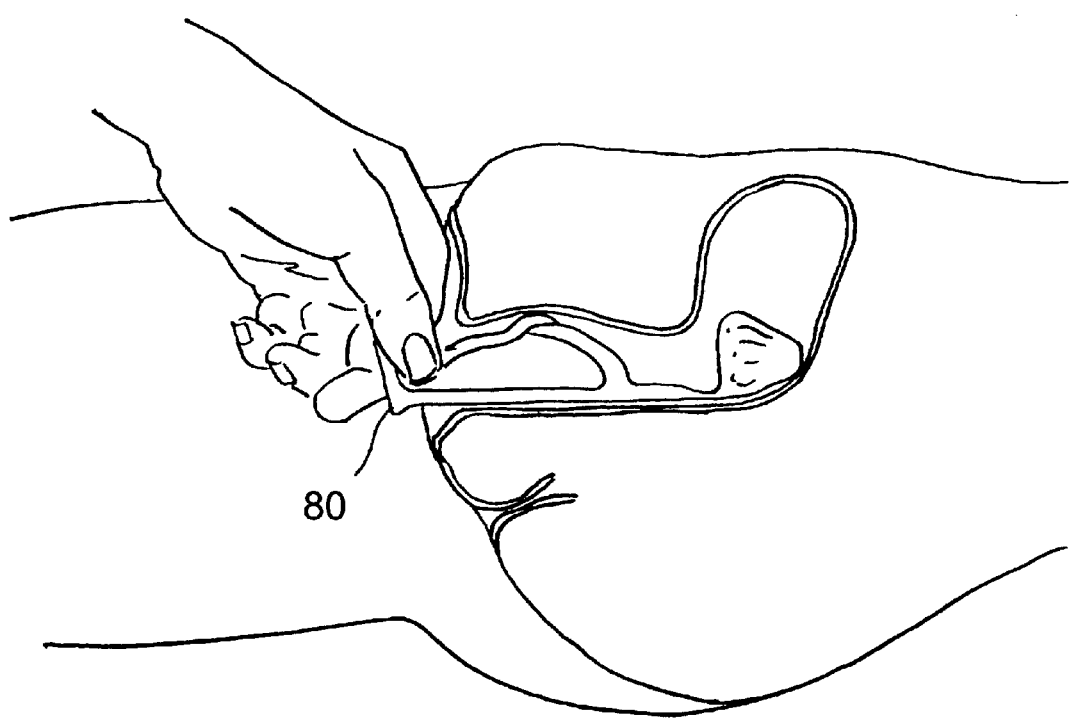
FIG. 12 illustrates a preferred method for removing the masculine brace according to the third preferred embodiment from the vagina of a woman.

The masculine brace 80 is installed and removed by pressing the raised tabs toward each other with the thumb 94 and the index finger 96 of a same hand as illustrated in FIG. 11 to enlarge the cylindrical cavity defined by the straps. The positions of the raised tabs 88, 90 adjacent the rear end of the splint member 22 are advantageous for removing the masculine brace 80 if desired once penetration is completed, as shown in FIG. 12. The positions of the raised tabs 88, 90 and of the thrust flange 92 are also advantageous because these parts project outside the partner's vagina at all times, thereby facilitating the removal of the masculine brace 80 during sexual intercourse if the need arises and the retrieving of the masculine brace 80 from the partner's vagina.

As to other material of construction, other manner of operation and methods of manufacture of the present invention, the same should be apparent from the above description and accompanying drawings and accordingly, further discussion relative to these aspects would be considered redundant and is not provided.

While three embodiments of the present invention have been illustrated in the accompanying drawings and described hereinabove, it will be appreciated by those skilled in the art that various modifications, alternate constructions and equivalents may be employed without departing from the true spirit and scope of the invention. Therefore, the above description and the illustrations should not be construed as limiting the scope of the present invention which is defined by the appended claims.

I claim:

1. A masculine brace for supporting a flaccid penis during sexual intercourse, comprising:

a stiff splint member having an elongated channel configuration, a rear end and a front end;

a first pair of straps extending from said rear end and jointly defining a rear circular clamp oriented transversely relative to said stiff splint member for clamping a penis at its base;

a second pair of straps extending from an intermediate region along said stiff splint member at a distance from said first pair of straps, and jointly defining a front circular clamp oriented transversely relative to said stiff splint member for clamping a penis at an intermediate region along said penis, and a bulb affixed to said front end of said stiff splint member, said bulb having a circular projection in line with said front and rear circular clamps;

such that said front and rear circular clamps are usable for holding said stiff splint member against a lower region of a penis for supporting said penis in an erected attitude, and said stiff splint member and said bulb are usable for simulating an action of an erected penis when said penis is affected by an erectile dysfunction affection.

2. The masculine brace as claimed in claim 1, wherein said splint member has a channel-shaped cross-section.

3. The masculine brace as claimed in claim 1, wherein said straps are integrally molded with said stiff splint member.

4. The masculine brace as claimed in claim 3, wherein each of said straps has a substantially semi-circular shape.

5. The masculine brace as claimed in claim 4, wherein said straps in each of said first and second pairs of straps extend beside each other in opposite directions.

6. The masculine brace as claimed in claim 4, wherein each said strap in each of said first and second pairs of straps has a rounded bulge formed on an end thereof.

7. The masculine brace as claimed in claim 1, wherein a material of construction thereof comprises a skeletal structure made of a rigid and resilient material and a coating made of a soft, smooth and sanitary material.

8. The masculine brace as claimed in claim 7, wherein said stiff and resilient material is stainless steel.

9. The masculine brace as claimed in claim 1, wherein a material of construction of said stiff splint member comprises a soft, non-irritating and non-absorbent plastic material.

10. The masculine brace as claimed in claim 9, wherein a material of construction of said straps in each said first and second pairs of straps comprises a soft, non-irritating, non-absorbent plastic material having a resilience and shape-memory properties.

11. The masculine brace as claimed in claim 10, wherein a material of construction of said bulb comprises a soft, non-irritating, non-absorbent and elastic material.

12. The masculine brace as claimed in claim 1, wherein all surfaces thereof are soft, smooth to the touch and free of crevice and sharp edge.

13. The masculine brace as claimed in claim 1 wherein said rear circular clamp has a rear clamping diameter and said front circular clamp has a front clamping diameter and said rear clamping diameter is slightly smaller than said front clamping diameter.

14. A masculine brace for supporting a flaccid penis during sexual intercourse, comprising:
- a stiff splint member having an elongated channel configuration, a rear end and a front end;
- a first pair of straps extending from said rear end and jointly defining a rear circular clamp oriented transversely relative to said stiff splint member for clamping a penis at its base;
- a second pair of straps extending from an intermediate region along said stiff splint member at a distance from said first pair of straps, and jointly defining a front circular clamp oriented transversely relative to said stiff splint member for clamping a penis at an intermediate region thereof, and
- a bulb affixed to said front end of said stiff splint member, said bulb having a circular projection in line with said front and rear circular clamps;
- said straps in said first and second pairs of straps comprising inside straps and outside straps, and said inside straps being joined to each other by a tendon,
- such that said front and rear circular clamps are usable for holding said stiff splint member against a lower region of a penis for supporting said penis in an erected attitude, said stiff splint member and said bulb are usable for simulating an action of an erected penis when said penis is affected by an erectile dysfunction affection, and said straps in said front and second pairs of straps are operable simultaneously using one hand.

15. The masculine brace as claimed in claim 14, wherein further comprising a pubis cushion mounted to one of said straps in said first pair of straps.

16. The masculine brace as claimed in claim 15, wherein said pubis cushion is made of a sponge-like material.

17. The masculine brace as claimed in claim 14, wherein all surfaces thereof are soft, smooth to the touch and free of crevice and sharp edge.

18. A masculine brace for supporting a flaccid penis during sexual intercourse, comprising:
- a stiff splint member having an elongated channel configuration, a front end, a rear end and an intermediate region between said front end and said rear end;
- first and second straps extending helically from said intermediate region of said stiff splint member in a cross-over arrangement toward said rear end of said stiff splint member; said first and second straps defining with said stiff splint member a cylindrical clamping cavity, for simultaneously clamping a penis along a mid-region and a base region thereof; and
- a bulb affixed to said front end of said stiff splint member, said bulb having a circular projection in line with said cylindrical clamping cavity;
- such that said first and second straps are usable for holding said stiff splint member against a lower region of a penis for supporting said penis in an erected attitude, said stiff splint member and said bulb are usable for simulating an action of an erected penis when said penis is affected by an erectile dysfunction affection, and said first and second straps are operable using one hand working near said rear end of said still splint member.

19. The masculine brace as claimed in claim 18, wherein each of said first and second straps has an end, and a raised tab on said end.

20. The masculine brace as claimed in claim 19, further having a U-shaped thrust flange mounted on said rear end of said stiff splint member, and said U-shaped thrust flange has less stiffness than said stiff splint member.

\* \* \* \* \*